(12) United States Patent
Shimko et al.

(10) Patent No.: US 12,004,791 B2
(45) Date of Patent: *Jun. 11, 2024

(54) BONE MATERIAL HYDRATION DEVICES AND METHODS

(71) Applicant: WARSAW ORTHOPEDIC INC., Warsaw, IN (US)

(72) Inventors: Daniel A. Shimko, Germantown, TN (US); Jared J. Diegmueller, Town and Country, MO (US); Jonathan M. Dewey, Memphis, TN (US); Kerem N. Kalpakci, Memphis, TN (US); Erick Vasquez, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,736

(22) Filed: Jan. 9, 2023

(65) Prior Publication Data
US 2023/0157740 A1  May 25, 2023

Related U.S. Application Data

(63) Continuation of application No. 17/031,335, filed on Sep. 24, 2020, now Pat. No. 11,564,723, which is a (Continued)

(51) Int. Cl.
*A61B 17/88* (2006.01)
*A61B 17/56* (2006.01)
(Continued)

(52) U.S. Cl.
CPC ...... *A61B 17/8833* (2013.01); *A61B 17/8816* (2013.01); *A61B 17/8825* (2013.01); (Continued)

(58) Field of Classification Search
CPC ............ A61B 17/8802; A61B 17/8805; A61B 17/8816; A61B 17/8825; A61B 17/8833; (Continued)

(56) References Cited

U.S. PATENT DOCUMENTS 3,514,791 A  6/1970 Sparks
4,706,418 A  11/1987 Stewart
(Continued)

FOREIGN PATENT DOCUMENTS

WO  2005/037136     4/2005
WO  2005037136 A2  4/2005

OTHER PUBLICATIONS

European Patent Office, 80298 Munich, Germany, Communication pursuant to Rules 70(2) and 70a(2) EPC, dated May 27, 2022 Supplementary European Search Report, Application No. 19854869.5, dated May 9, 2022.

(Continued)

*Primary Examiner* — Larry E Waggle, Jr.
(74) *Attorney, Agent, or Firm* — Sorell, Lenna & Schmidt, LLP

(57) ABSTRACT

A device for hydrating particulate bone material is provided. The device comprises a tubular member having an interior surface and an exterior surface. The interior surface is configured to receive the particulate bone material and a hydration fluid. The exterior surface has a plurality of pores configured to allow the hydration fluid to flow into the interior surface of the tubular member and hydrate the particulate bone material. The plurality of pores are smaller in size than the particulate bone material. Methods of dispensing particulate the bone material are also provided.

16 Claims, 8 Drawing Sheets

Related U.S. Application Data continuation of application No. 16/116,212, filed on Aug. 29, 2018, now Pat. No. 10,813,676.

(51) Int. Cl.
  *A61F 2/28* (2006.01)
  *A61F 2/46* (2006.01)

(52) U.S. Cl.
  CPC .............. *A61F 2/28* (2013.01); *A61F 2/4601* (2013.01); *A61B 2017/564* (2013.01); *A61B 2017/8838* (2013.01); *A61F 2002/2835* (2013.01)

(58) Field of Classification Search
  CPC ..... A61B 2017/8838; A61F 2002/2835; A61F 2/46; A61F 2/4601
  See application file for complete search history.

(56) References Cited

U.S. PATENT DOCUMENTS

| | | | |
|---|---|---|---|
| 4,787,906 A | 11/1988 | Haris | |
| 5,016,628 A | 5/1991 | Lambert | |
| 5,462,117 A | 10/1995 | Green et al. | |
| 6,723,131 B2* | 4/2004 | Muschler | A61L 27/425 623/23.51 |
| 7,172,071 B2* | 2/2007 | Hawkins | A61F 2/4601 206/438 |
| 7,208,015 B2 | 4/2007 | Pointillart et al. | |
| 7,794,449 B2* | 9/2010 | Shippert | A61M 1/774 604/38 |
| 8,622,739 B2 | 1/2014 | Karmon | |
| 9,034,052 B2* | 5/2015 | Shimko | A61F 2/4601 623/23.54 |
| 9,220,598 B2 | 12/2015 | Betz et al. | |
| 9,427,335 B2 | 8/2016 | Ponticiello et al. | |
| 9,492,278 B2 | 11/2016 | Wei et al. | |
| 9,623,148 B2 | 4/2017 | Partee et al. | |
| 10,813,676 B2* | 10/2020 | Shimko | A61F 2/4644 |
| 11,564,723 B2* | 1/2023 | Shimko | A61F 2/28 |
| 2002/0161449 A1 | 10/2002 | Muschler | |
| 2005/0186375 A1 | 8/2005 | Neter et al. | |
| 2006/0083769 A1 | 4/2006 | Kumar et al. | |
| 2008/0260598 A1 | 10/2008 | Gross et al. | |
| 2009/0116907 A1 | 5/2009 | Altirriba | |
| 2010/0076480 A1 | 3/2010 | Lu et al. | |
| 2017/0027684 A1 | 2/2017 | Schmieding et al. | |

OTHER PUBLICATIONS

European Search Report dated May 9, 2022 by the European Patent Office in corresponding European application No. 19854869.5 for Bone Material Hydration Devices and Methods.

First Office Action issued by the Chinese National IP Administration dated Jan. 6, 2022 in corresponding Chinese 1 Patent Application No. 201980055869.7 for Bone Material Hydration Devices and Methods.

\* cited by examiner

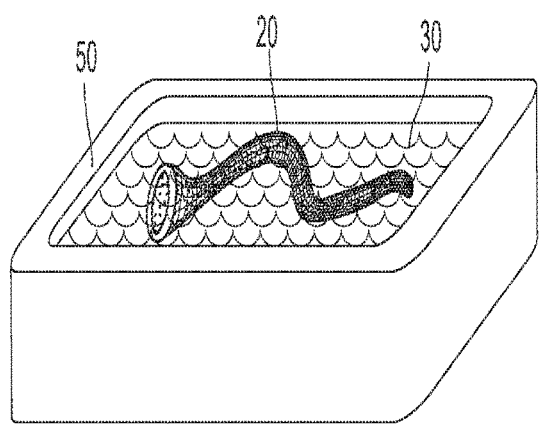
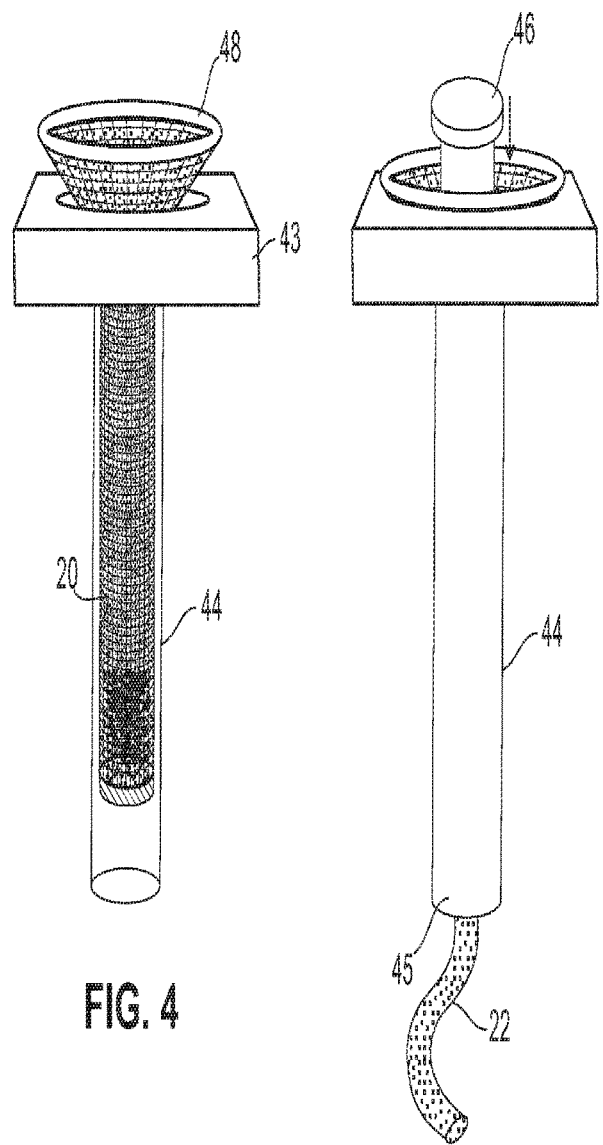
FIG. 3
FIG. 4
FIG. 5

BONE MATERIAL HYDRATION DEVICES AND METHODS

BACKGROUND

The use of bone material including natural bone and bone substitute materials for filling a bone repair site in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. A bone graft can be made from various bone particulate having various particle sizes, such as, for example, fine bone particulate. However, handling of fine particulate bone material can be difficult due to its consistency. In order to insert the bone material, it is common to use a delivery instrument.

Currently, there are various delivery instruments used for bone material delivery, however, not many instruments can handle bone material when the bone material is fine particulate bone material. Further, the bone material can be difficult to package and re-hydrate. Components of the bone material can also be wasted during the packaging and re-hydrating process and allow contamination of the bone material during packing and hydration of the bone material as a result of several manipulating steps.

Therefore, it would be beneficial to provide devices for effectively hydrating particulate bone material which can be used for administering the particulate bone material to a surgical site. Methods of hydrating and kits to hydrate bone material would also be beneficial.

SUMMARY

Devices and methods are provided for hydrating particulate bone material. The hydrated particulate bone material can be delivered to a surgical site via a delivery instrument. The device packs, hydrates and delivers particulate bone material. In one embodiment, a device for hydrating particulate bone material is provided. The device comprises a tubular member having an interior surface and an exterior surface. The interior surface is configured to receive the particulate bone material and a hydration fluid. The exterior surface has a plurality of pores configured to allow the hydration fluid to flow into the interior surface of the tubular member and hydrate the particulate bone material. The plurality of pores are smaller in size than the particulate bone material.

In some embodiments, a device for hydrating particulate bone material is provided. The device comprises a tubular member having an interior surface configured to receive the particulate bone material and a hydration fluid. The tubular member includes a proximal end opening configured to receive a syringe, and a distal end opening configured to receive a cap. The cap has a plurality of pores configured to allow the hydration fluid to flow into the interior surface of the tubular member and hydrate the particulate bone material. The plurality of pores on the cap are smaller in size than the particulate bone material.

In some embodiments, a method of dispensing particulate bone material at a surgical is provided. The method comprises loading a device for hydrating the particulate bone material, the device comprising a tubular member having an interior surface and an exterior surface, the interior surface configured to receive the particulate bone material and a hydration fluid, the exterior surface having a plurality of pores configured to allow the hydration fluid to flow into the interior surface of the tubular member and hydrate the particulate bone material, the plurality of pores being smaller in size than the particulate bone material; immersing the device in a fluid filled bath; and engaging the device with a cannula and a plunger to dispense the particulate bone material to the surgical site.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

The present disclosure will become more readily apparent from the specific description accompanied by the following drawings, in which:

FIG. 3 is a perspective view of the device of FIG. 1 immersed in a fluid filled bath to hydrate the bone material.

FIG. 4 is a front view of the device of FIG. 1 after hydration in the fluid filled bath of FIG. 3. In this embodiment, the device is disposed with a delivery instrument. The collar of the device matingly engages with an end of the delivery instrument.

FIG. 5 is a front view of the bone material delivery device of FIG. 4 disposed with the delivery instrument. In this embodiment, a plunger is inserted at the proximal end of the device and into the delivery instrument to dispense the bone material to a surgical site.

FIG. 9 shows the plunger of FIG. 7 engaging with the proximal end of the device and the syringe of FIG. 8 engaging with the port of the device. The plunger of the syringe is moved in an upward direction to draw air and/or fluid out of the tubular member, thereby creating negative pressure in the tubular member. The plunger is then moved in a downward direction such that the hydrated particulate bone material is dispensed from the tubular member.

Figure 1:
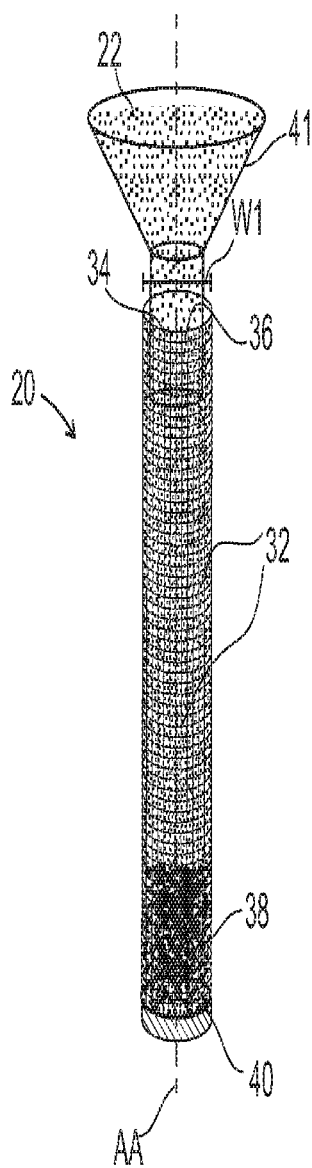
FIG. 1 is a front view of one embodiment of a device for hydrating a particulate bone material. The device comprises a tubular member having an interior surface configured to receive the particulate bone material and a hydration fluid. The tubular member also includes an exterior surface having a plurality of pores configured to allow the hydration fluid to flow into the interior surface of the tubular member and hydrate the particulate bone material. The plurality of pores are smaller in size than the particulate bone material. The tubular member comprises a proximal end opening configured to receive the bone material and a removable distal end configured to form a distal end opening to dispense the particulate bone material. In this embodiment, the device is shown engaging with a funnel and being loaded with the bone material.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, for example, 5.5 to 10.

The bone material can have a bioactive agent mixed with it. Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in Pharmaceutical Substances: Syntheses, Patents, Applications by Axel Kleemann and Jurgen Engel, Thieme Medical Publishing, 1999; Merck Index: An Encyclopedia of Chemicals, Drugs, and Biologicals, edited by Susan Budavari et al., CRC Press, 1996; and United States Pharmacopeia-25/National Formulary-20, published by the United States Pharmacopeia Convention, Inc., Rockville Md., 2001, each of which is incorporated herein by reference. In some embodiments, bioactive agents include nutrients, oxygen sources, and hypoxic inducers such as carbon monoxide or iron chelators.

Biocompatible, as used herein, is intended to describe materials that, upon administration in vivo, do not induce undesirable long-term effects.

Bone material includes material derived from natural bone and/or synthetic bone. Synthetic bone includes, but is not limited to biomaterials that contain hydroxyapatite, calcium phosphate, silicate materials, cements, polymers, collagen sheets, fibers, granules, alginate, starch, and/or PLGA. In some embodiments, the bone material can be ceramic/synthetic bone void fillers and can contain animal derived collagen elements. In some embodiments, various MasterGraft® products produced by Medtronic Sofamor Danek, Inc., Memphis, Tenn can be used as the bone material. The bone material can be in particulate form such as, for example, chips, fibers, powder or a combination thereof. Bone, as used herein, refers to bone that is cortical, cancellous or cortico-cancellous of autogenous, allogenic, xenogenic, or transgenic origin.

Demineralized, as used herein, refers to any material generated by removing mineral material from tissue, for example, bone tissue. In certain embodiments, demineralized bone material may be added to the bone void filler. The demineralized bone material described herein include preparations containing less than 5%, 4%, 3%, 2% or 1% calcium by weight. Partially demineralized bone (for example, preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," "superficially demineralized," and "fully demineralized." In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone material can comprise demineralized material.

Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (for example, preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 and/or 1000:1. In overall appearance, the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are demineralized, however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. The non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular."

Percutaneous, as used herein, refers to a surgical method where entry to the spine is by puncture or minor incision, of instrumentation through the skin or mucous membrane and/or any other body layers necessary to reach the site of the procedure.

The devices, bone materials, kits and methods may be employed to treat spinal disorders such as, for example, degenerative disc disease, disc herniation, osteoporosis, spondylolisthesis, stenosis, scoliosis and other curvature abnormalities, kyphosis, tumor and fractures. The devices, bone materials, kits and methods may be employed with other osteal and bone related applications, including those associated with diagnostics and therapeutics. They may also be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The devices, bone materials, kits and methods may also be alternatively employed with procedures for treating the lumbar, cervical, thoracic, sacral and pelvic regions of a spinal column. They may also be used on animals, bone models and other non-living substrates, such as, for example, in training, testing and demonstration.

In various embodiments, the bone material comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the devices, bone materials, kits and methods are used in minimally invasive surgeries and the bone material is percutaneously delivered to a surgical site or the surgical site is the posterior spine.

Devices

Referring to FIGS. 1 to 5, a device 20 is provided for hydrating particulate bone material 22 (e.g., bone graft). The device is configured to hydrate the particulate bone material prior to loading of the particulate bone material into a delivery instrument. The hydrated particulate bone material is fully contained in the device and is then loaded into a delivery instrument for administration to a surgical site.

Figure 2:
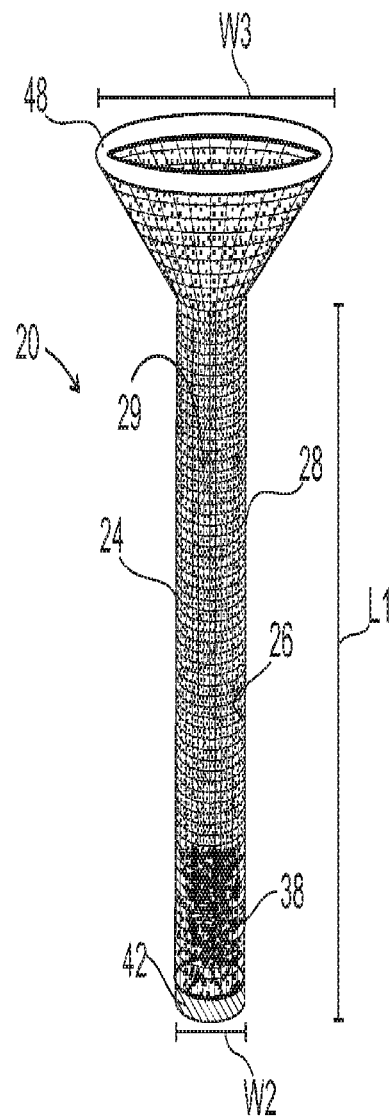
FIG. 2 is front view of the device of FIG. 1. In this embodiment, the device includes a rigid collar to facilitate loading and attachment to bone delivery instruments.

The device includes a tubular member 24 having an interior surface 26 and an exterior surface 28, as shown in FIG. 2. The interior surface defines a channel 29 and is configured to receive the particulate bone material and a hydration fluid 30. The exterior surface of the tubular member includes a plurality of pores 32 configured to allow the hydration fluid to flow into the interior surface of the tubular member and hydrate the particulate bone material, as described herein. The plurality of pores are smaller in size than the particulate bone material. In some embodiments, the plurality of pores have a pore size from about 10 to about 100 microns, from about 20 to about 80 microns, or from about 40 to about 60 microns. In some embodiments, the plurality of pores can have a pore size from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98 to about 100 microns. In some embodiments, the plurality of pores can be the same or various sizes throughout the tubular member, the plurality of pores can be larger when disposed at a distal end, can be uniform throughout or can be larger in distinct zones on the exterior surface of the tubular member.

In some embodiments, when the bone material contained in the tubular member is fibrous instead of particulate, the plurality of pores can be made larger than the diameter of the fibers but smaller than the overall length of the fibers, thus restricting the fibers from exiting through the plurality of pores. In some embodiments, when the bone material is fibrous, the longer the fibers, the more entangled the fibers will become, therefore further preventing the fibers from exiting through the plurality of pores which enables the plurality of pores to be even larger than if the bone material was made from particulate bone.

In some embodiments, when a specific level of hydration is required for the bone material, the plurality of pores can be used to evacuate surplus hydration.

In some embodiments, the plurality of pores can be a circular hole or holes where a plug or plugs (not shown) of the tubular member has been removed. In some embodiments, the plurality of pores can be a cut or cuts in a side of the tubular member to break tubular member continuity. The cut or cuts can be a single point break, such as a pin prick, a horizontal, vertical or angled slit formed by slicing the tubular member, or semi-circular patterns cut into the tubular member to form flaps. The flaps can be biased into a particular direction to facilitate hydration or flow of bone material when the bone material is dispensed from the tubular member.

In some embodiments, the plurality of pores can be one-way pores such that fluid is permitted to enter the tubular member, but then, as a plunger is used to dispense the bone material, the plurality of pores can close to prevent the bone material or fluid from exiting through the plurality of pores. This would also allow pressurization of the bone material in the tubular member, and allow more intimate hydration of the bone material.

The tubular member comprises a proximal end 34 defining a proximal end opening 36, a distal end 38 defining a distal end opening 40 and a longitudinal axis AA disposed therebetween. The proximal end opening is configured to receive the particulate bone material and the distal end opening is configured to dispense the particulate bone material.

The tubular member can have a length L1, a width W1 at the proximal end and a width W2 at the distal end. The length L1 can be from about 1 inch to about 20 inches, from about 1 to about 15 inches, from about 1 to about 10 inches, from about 1 to about 5 inches, from about 5 to about 20 inches, from about 5 to about 15 inches, from about 5 to about 10 inches, from about 10 to about 20 inches, from about 10 to about 15 inches, or from about 15 to about 20 inches. In some embodiments, the length L1 can be from about 1, 2, 3, 4, 5, 6, 7, 8, 9, 10, 11, 12, 13, 14, 15, 16, 17, 18, 19 to about 20 inches.

In some embodiments, widths W1 and W2 can be from about 0.5 to about 5 inches, from about 1 inch to about 5 inches, from about 1 to about 4 inches, from about 1 to about 3, from about 1 to about 2 inches, from about 2 to about 5 inches, from about 2 to about 4 inches, from about 2 to about 3 inches, from about 3 to about 5 inches or from about 4 to about 5 inches. In some embodiments, widths W1 and W2 can be from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about 5 inches. In some embodiments, widths W1 and W2 can be the same or different sizes.

The tubular member comprises a removable distal end 42 configured to form the distal end opening to dispense the particulate bone material. In some embodiments, the removable distal end can be a sealed end. The sealed end can be sealed via heat and/or adhesive. In some embodiments, the sealed end can be sealed via adhesives including, but not limited to cyanoacrylates (such as histoacryl, B Braun, which is n-butyl-2 cyanoacrylate; or Dermabond, which is 2-octylcyanoacrylate), epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance.

In some embodiments, the removable distal end forms the distal end opening via mechanical means such as via cutting or tearing the distal end of the tubular member with scissors and/or a blade.

In some embodiments, the particulate bone material can be loaded into the device from the proximal end opening of the tubular member via a funnel 41 or other loading instrument, as shown in FIG. 1. The funnel engages the proximal end opening of the tubular member and the particulate bone material is loaded into the channel of the tubular member.

The tubular member of the device is configured to slidably engage with a proximal end 43 of a cannula 44, and the proximal end opening and channel of the tubular member is configured to slidably receive a plunger 46, as shown in FIGS. 4 and 5 for administration of the particulate bone material to a surgical site once the particulate bone material is hydrated via the device. As described below, the device is immersed in a fluid filled bath 50 to hydrate the particulate bone material that is loaded into the tubular member. Once hydrated, the particulate bone material will be dispensed out of a distal end opening 45 of the cannula into a surgical site.

In some embodiments, the proximal end opening of the tubular member comprises a collar 48 that is configured to engage with the proximal end of the cannula, as shown in FIG. 4. The collar will be flush or resting on a surface of the proximal end of the cannula. In some embodiments, the proximal end of the cannula can include a collar configured to engage with the tubular member. In some embodiments, the collar is a rigid funnel. In some embodiments, when the proximal end opening includes a collar, the collar has a width W3 that is greater than width W1. In some embodiments, width W3 is from about 0.5 to about 5 inches, from about 1 inch to about 5 inches, from about 1 to about 4 inches, from about 1 to about 3, from about 1 to about 2 inches, from about 2 to about 5 inches, from about 2 to about 4 inches, from about 2 to about 3 inches, from about 3 to about 5 inches or from about 4 to about 5 inches. In some embodiments, width W3 can be from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about 5 inches.

In some embodiments, the tubular member comprises a mesh and/or a straw. In some embodiments, the mesh can be made from a natural and/or synthetic material.

In some embodiments, the tubular member is moldable or flexible. In some embodiments, the tubular member is flexible and elastic, which allows the tubular member to be kneaded while in the fluid filled bath. In this embodiment, if the tubular member is compressed, any air contained within the tubular member will be pushed out through the pores. When the tubular member elastically returns to its original shape, the tubular member will draw in fluid, thereby hydrating the contained bone material. In some embodiments, the tubular member has a modulus of elasticity from about from about $1\times-10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In some embodiments, the tubular member is flexible but relatively inelastic, such that the tubular member does not return to its original shape easily. In this embodiment, the tubular member being flexible but relatively inelastic would allow the tubular member to be hydrated in a smaller fluid filled bath by allowing the tubular member to be coiled on itself, as well as would allow less manipulation by the surgeon when positioning in-situ before dispensing the bone material.

In some embodiments, the tubular member can be rigid. A rigid tubular member facilitates easy attachment of a delivery tip (not shown) onto the tubular member, allows the tubular member to be easily moved through the funnel and/or allows the device to be used without a delivery instrument. In some embodiments, portions of the tubular member can be flexible, while other portions can be rigid.

In some embodiments, the tubular member can be made from a material that is flexible when dry but becomes rigid when hydrated. In this embodiment, the transition of the material from flexible to rigid can occur over a period of time, such as after the device is immersed in the fluid filled bath. In some embodiments, the tubular member can initially be rigid and then can become softer and more flexible as the tubular member is soaked.

As described above, the device is immersed in a fluid filled bath 50 to hydrate the particulate bone material. In some embodiments, the device is fully immersed in the fluid filled bath for an amount of time. In some embodiments, the device is fully immersed in the fluid filled bath from about 10 seconds to about 24 hours, depending on the composition of the particulate bone material and the fluid. In some embodiments, the device is fully immersed in the fluid filled bath from about 10, 15, 20, 25, 30, 35, 40, 45, 50, 55 seconds, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 minutes, 2, 3, 4, 5, 6, 7, 8, 9, 10, 11, 12, 13, 14, 15, 16, 17, 18, 19, 20, 21, 22, 23 to about 24 hours.

In some embodiments, the fluid can be blood, bone marrow aspirate, mesenchymal stem cells, sterile water, dextrose, other sugars including but not limited to sucrose, fructose, glucose, lactated ringer's, polyols including, but not limited to, mannitol, xylitol, sorbitol, maltitol, lactitol, polysaccharides including, but not limited to, native or pre-gelatinized starch, maltodextrins, cyclodextrins, mineral compounds including, but not limited to, dicalcium or tricalcium phosphate, either dihydrate or anhydrous, cellulose derivatives including, but not limited to, microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline, 0.45% saline or phosphate buffered saline. In some embodiments, other fluids can be used for example, D5W (dextrose in 5% water), D5NS (dextrose in 5% water and normal saline) and D5W/½NS (D5W and ½ normal saline), lactated Ringer solution or the like.

In some embodiments, the particulate bone material is in a powder or a wet form and has a particle size of 250 microns or less. In some embodiments, the particulate bone material is demineralized bone (DBM).

In some embodiments, the tubular member of the device can be pre-packed with the particulate bone material from a manufacturer with the proximal end and the distal end of the tubular member sealed. The ends can then be cut prior to use and administration.

Referring to FIGS. 6-9, a device 200, similar to device 20 above, is provided for hydrating particulate bone material. The device is configured to hydrate the particulate bone material before administration of the particulate bone material to a surgical site. The hydrated particulate bone material is fully contained in the device and after hydration, the device ejects the particulate bone material at the surgical site.

Figure 6:
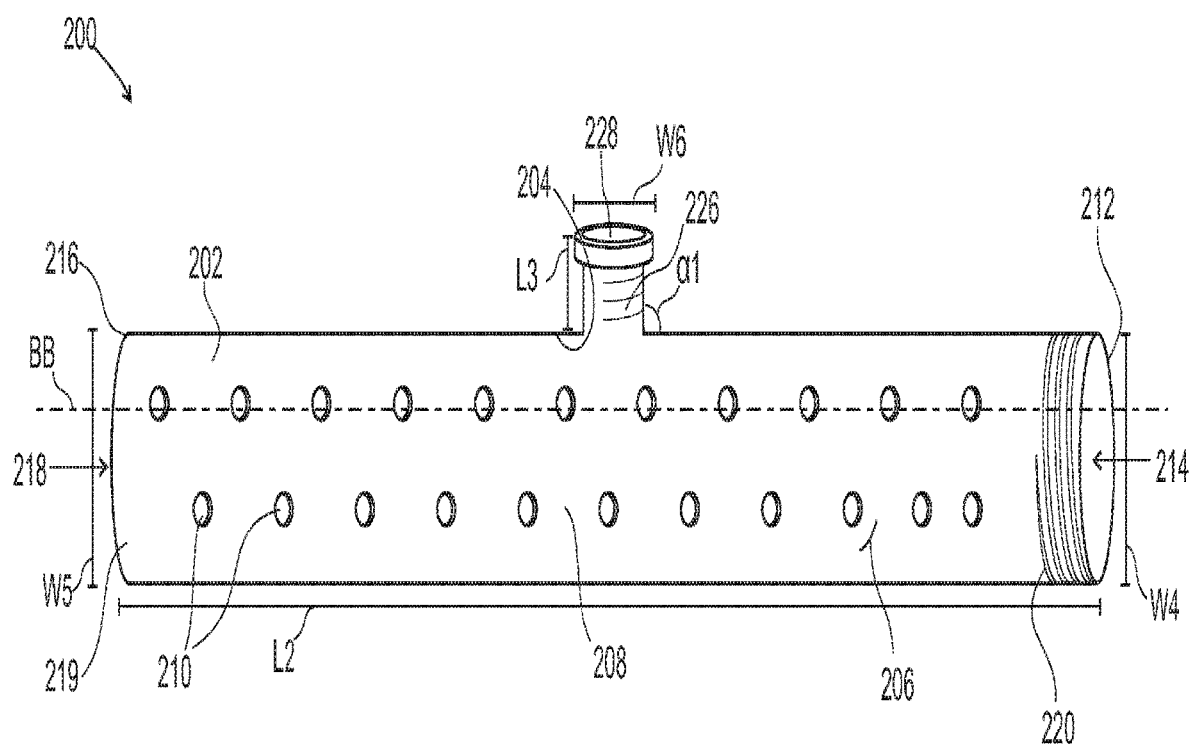
FIG. 6 is a side view of one embodiment of a device for hydrating a particulate bone material. In this embodiment, the tubular member of the device comprises a one-way valve and a port configured to receive a syringe. Further, the interior surface of the tubular member at a proximal end comprises threading to engage with a threaded outer surface of a plunger.

The device includes a tubular member 202, similar to tubular member 24, having an interior surface 204 and an exterior surface 206, as shown in FIG. 6. The interior surface defines a channel 208 and is configured to receive the particulate bone material and a hydration fluid 30. The exterior surface of the tubular member includes a plurality of pores 210 configured to allow the hydration fluid to flow into the interior surface of the tubular member and hydrate the particulate bone material. The plurality of pores are smaller in size than the particulate bone material. In some embodiments, the plurality of pores have a pore size from about 10 to about 100 microns, from about 20 to about 80 microns, or from about 40 to about 60 microns. In some embodiments, the plurality of pores can have a pore size from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98 to about 100 microns. In some embodiments, the plurality of pores can be the same or various sizes throughout the tubular member, the plurality of pores can be larger when disposed at a distal end, can be uniform throughout, as shown in FIG. 6 or can be larger in distinct zones on the exterior surface of the tubular member. In some embodiments, the tubular member is mesh and/or a straw, as described above with regard to device 20. In some embodiments, the tubular member can be flexible.

The tubular member comprises a proximal end 212 defining a proximal end opening 214, a distal end 216 defining a distal end opening 218 and a longitudinal axis BB disposed therebetween. The proximal end opening is configured to receive the particulate bone material and the distal end opening is configured to dispense the particulate bone material. In some embodiments, a removable distal end 219 forms the distal end opening via mechanical means such as via cutting or tearing the distal end of the tubular member with scissors and/or a blade.

The tubular member can have a length L2, a width W4 at the proximal end and a width W5 at the distal end. The length L2 can be from about 1 inch to about 20 inches, from about 1 to about 15 inches, from about 1 to about 10 inches, from about 1 to about 5 inches, from about 5 to about 20 inches, from about 5 to about 15 inches, from about 5 to about 10 inches, from about 10 to about 20 inches, from about 10 to about 15 inches, or from about 15 to about 20 inches. In some embodiments, the length L2 can be from about 1, 2, 3, 4, 5, 6, 7, 8, 9, 10, 11, 12, 13, 14, 15, 16, 17, 18, 19 to about 20 inches.

In some embodiments, widths W4 and W5 can be from about 0.5 to about 5 inches, from about 1 inch to about 5 inches, from about 1 to about 4 inches, from about 1 to about 3, from about 1 to about 2 inches, from about 2 to about 5 inches, from about 2 to about 4 inches, from about 2 to about 3 inches, from about 3 to about 5 inches or from about 4 to about 5 inches. In some embodiments, widths W4 and W5 can be from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about 5 inches. In some embodiments, widths W4 and W5 can be the same or different sizes.

Figure 7:
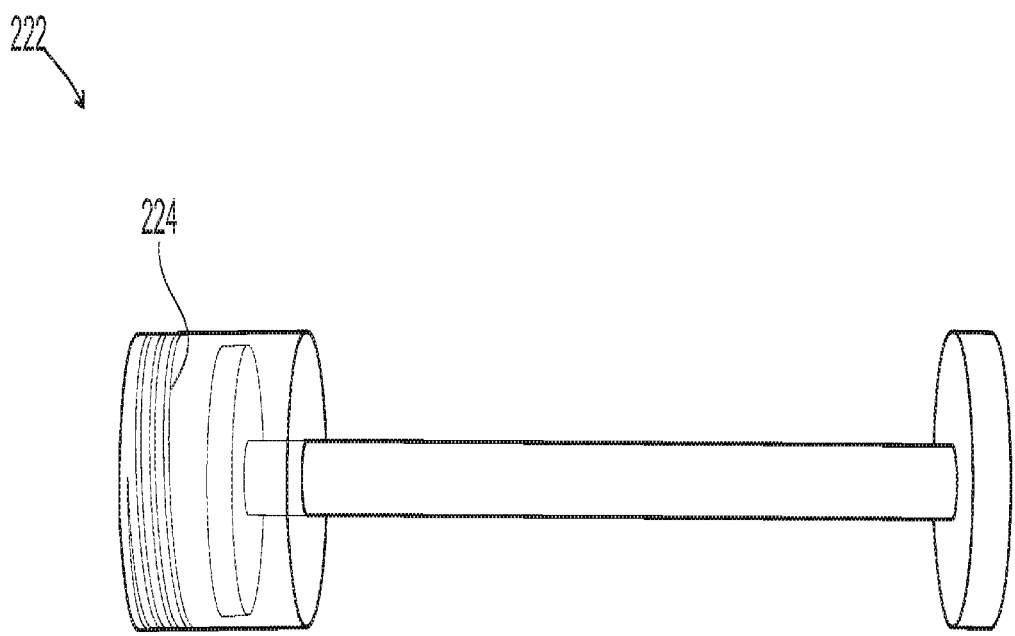
FIG. 7 is a side view of the plunger that engages with the device of FIG. 6.
Figure 9:
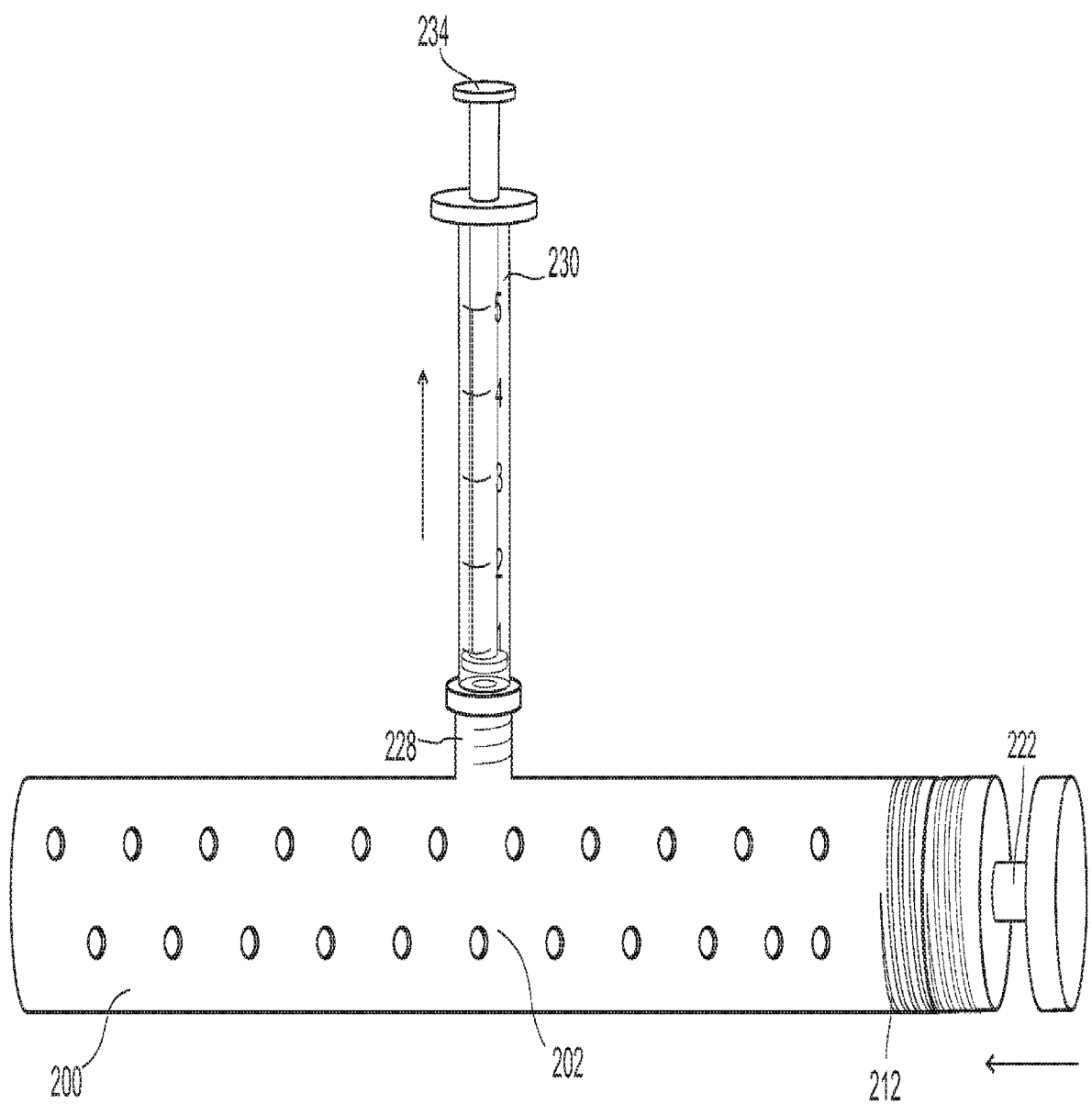
FIG. 9 is a side view of the device of FIG. 6.

The interior surface of the tubular member at the proximal end includes threading 220 that engages with a threaded outer surface 224 of a plunger 222, as shown in FIGS. 7 and 9. In some embodiments, the threading can be angled, horizontal or partially threaded. Engagement of the tubular member and the plunger facilitates dispensing of the particulate bone material.

Figure 8:
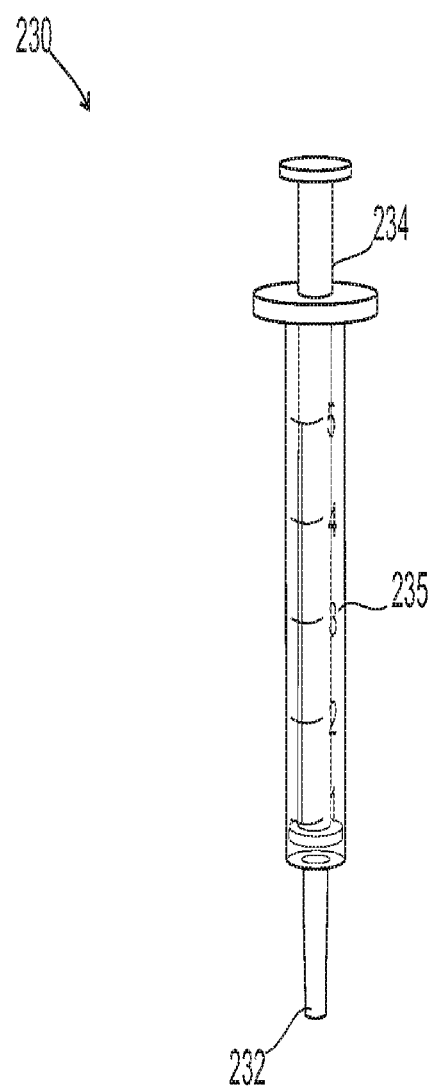
FIG. 8 is a front view of the syringe that engages with the port of the device of FIG. 6.

The tubular member includes a valve 226 and a port 228 that is configured to receive a syringe 230 having a barrel 235, as shown in FIGS. 8 and 9. For example, a distal end or tip 232 of the syringe engages with the port 228 and a user can move a syringe plunger 234 in an upward direction to draw air and/or fluid out of the tubular member and into the syringe barrel such that a vacuum is formed. Negative pressure will be created in the tubular member. In some embodiments, the valve can be a one-way valve, such that any vacuum introduced would remain after the syringe is removed.

The port has a length L3 and a width W6. In some embodiments, the length L3 is from about 0.5 to about 5 inches, from about 1 to about 4 inches, or from about 2 to about 3 inches. In some embodiments, the length L3 is from about 0.5, 1, 2, 3, 4 to about 5 inches. In some embodiments, the port is disposed perpendicular to the tubular member and has an angle α1. In some embodiments, angle α1 is from about 20 to 60 degrees. In some embodiments, angle α1 is from about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60 degrees.

The device is immersed in the fluid filled bath 50 shown in FIG. 3 to hydrate the particulate bone material. In some embodiments, the device is fully immersed in the fluid filled bath for an amount of time. In some embodiments, the device is fully immersed in the fluid filled bath from about 10 seconds to about 24 hours, depending on the composition of the particulate bone material and the fluid. In some embodiments, the device is fully immersed in the fluid filled bath from about 10, 15, 20, 25, 30, 35, 40, 45, 50, 55 seconds, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 minutes, 2, 3, 4, 5, 6, 7, 8, 9, 10, 11, 12, 13, 14, 15, 16, 17, 18, 19, 20, 21, 22, 23 to about 24 hours. In some embodiments, while the device is immersed in the fluid filled bath, the proximal end or tip of the syringe is attached to the device via engagement with the port. As shown in FIG. 9, the user then moves the syringe plunger in an upward direction to create a vacuum to draw fluid from the fluid filled bath into the tubular member to hydrate the bone material. Negative pressure is then created in the tubular member. The device is then removed from the fluid filled bath and the syringe is disengaged from the port. The plunger is then attached to the proximal end opening of the tubular member and the plunger is moved in a downward direction to dispense the hydrated particulate bone material out of the distal end opening of the tubular member and into a surgical site. In some embodiments, fluid can be inserted into the device through the port.

In some embodiments, the tubular member can be packed with the bone material under a vacuum such that as the tubular member is opened/cut/placed in the fluid filled bath, the internal vacuum will draw up the fluid, thus removing the need to draw the fluid into the tubular member externally by using a syringe.

Figure 10:
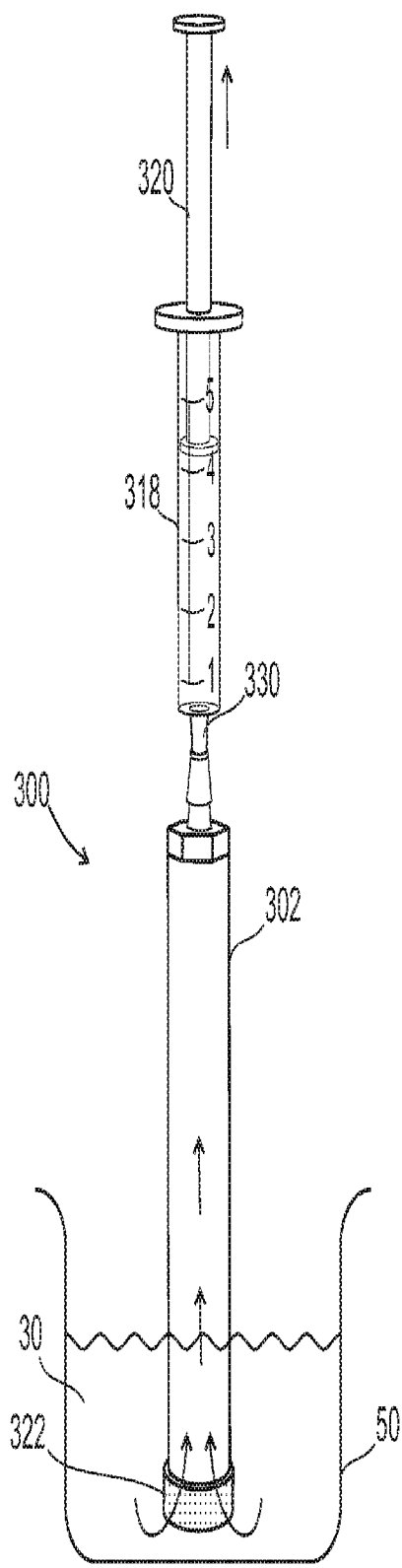
FIG. 10 is a front view of one embodiment of a device for hydrating a bone material. The device comprises a tubular member having an interior surface configured to receive the particulate bone material and a hydration fluid. The tubular member includes a proximal end opening configured to receive a syringe, and a distal end opening configured to receive a cap. The cap including a plurality of pores configured to allow the hydration fluid to flow into the interior surface of the tubular member and hydrate the particulate bone material. The plurality of pores are smaller in size than the particulate bone material. In this embodiment, the proximal end opening engages with a cap comprising a luer fitting that engages with the syringe. The cap including a plurality of pores will draw fluid from a fluid filled bath into the pores of the cap and into the device when the syringe is moved in an upward direction to hydrate the bone material.
Figure 11:
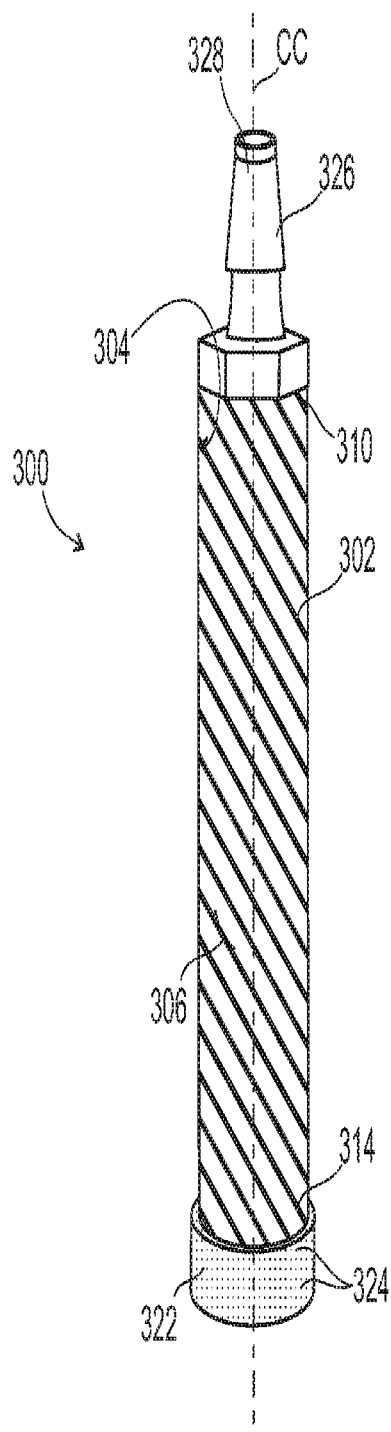
FIG. 11 is a front view of the bone material delivery device of FIG. 10. In this embodiment, the syringe and caps are removed from both ends of the device.
Figure 12:
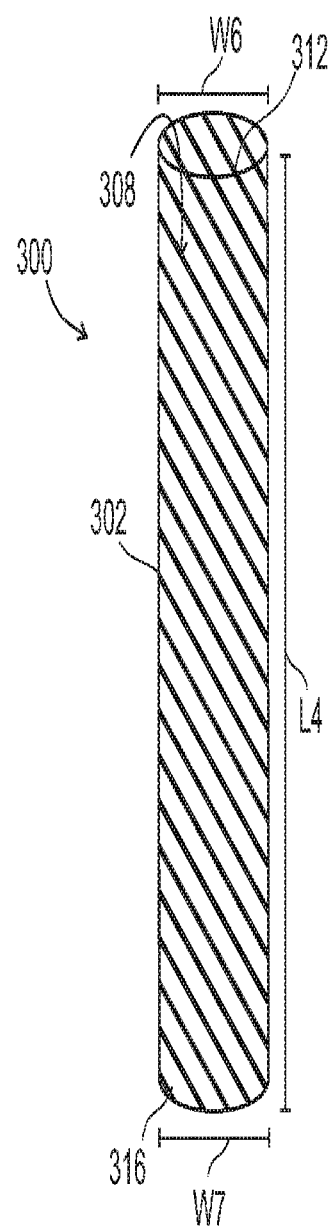
FIG. 12 is a front view of the bone material delivery device of FIG. 10 where the device is ready to be loaded into a delivery instrument for delivery of the bone material to a surgical site.

Referring to FIGS. 10-12, a device 300, similar to devices 20 and 200 above, is provided for hydrating particulate bone material. The device is configured to hydrate the particulate bone material prior to loading of the particulate bone material into a delivery instrument. The hydrated particulate bone material is fully contained in the device and is then loaded into a delivery instrument for administration to a surgical site.

The device comprising a tubular member 302, similar to tubular members 24 and 202, having an interior surface 304 and an exterior surface 306, as shown in FIG. 11. The interior surface defines a channel 308 and is configured to receive the particulate bone material 22 and hydration fluid 30. The tubular member includes a proximal end 310 defining a proximal end opening 312, a distal end 314 defining a distal end opening 316 and a longitudinal axis CC disposed therebetween. In some embodiments, the tubular member comprises a straw.

The proximal end opening is configured to receive the particulate bone material and the distal end opening is configured to dispense the particulate bone material. The proximal end opening is configured to receive a syringe 318 having a syringe plunger 320, and the distal end opening is configured to receive a cap 322. In some embodiments, the syringe is a standard or vacuum lock syringe.

The tubular member can have a length L4, a width W6 at the proximal end and a width W7 at the distal end. The length L4 can be from about 1 inch to about 20 inches, from about 1 to about 15 inches, from about 1 to about 10 inches, from about 1 to about 5 inches, from about 5 to about 20 inches, from about 5 to about 15 inches, from about 5 to about 10 inches, from about 10 to about 20 inches, from about 10 to about 15 inches, or from about 15 to about 20 inches. In some embodiments, the length L4 can be from about 1, 2, 3, 4, 5, 6, 7, 8, 9, 10, 11, 12, 13, 14, 15, 16, 17, 18, 19 to about 20 inches.

In some embodiments, widths W6 and W7 can be from about 0.5 to about 5 inches, from about 1 inch to about 5 inches, from about 1 to about 4 inches, from about 1 to about 3, from about 1 to about 2 inches, from about 2 to about 5 inches, from about 2 to about 4 inches, from about 2 to about 3 inches, from about 3 to about 5 inches or from about 4 to about 5 inches. In some embodiments, widths W6 and W7 can be from about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about 5 inches. In some embodiments, widths W6 and W7 can be the same or different sizes.

The cap includes a plurality of pores 324 configured to allow the hydration fluid to flow into the interior surface of the tubular member and hydrate the particulate bone material. The plurality of pores are smaller in size than the particulate bone material. In some embodiments, the plurality of pores have a pore size from about 10 to about 100 microns, from about 20 to about 80 microns, or from about 40 to about 60 microns. In some embodiments, the plurality of pores can have a pore size from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98 to about 100 microns. In some embodiments, the plurality of pores can be the same or various sizes throughout the cap, can be uniform throughout, or can be larger in distinct zones on the cap.

The proximal end opening of the tubular member engages with a cap 326 that includes a luer fitting 328 that engages with a distal end 330 of the syringe.

Once the proximal end opening of the tubular member engages with the cap having the luer fitting, the distal end of the syringe is engaged with the luer fitting. The tubular member at the distal end/cap is immersed in the fluid filled bath 50 shown in FIG. 10. The syringe plunger is moved in an upward direction to create a vacuum which draws the fluid from the bath into the plurality of pores of the cap and up the channel of the tubular member to hydrate the particulate bone material. As shown in FIGS. 11 and 12, the caps are then removed from the ends of the tubular member and the device can then be loaded into a delivery instrument so that the hydrated particulate bone material can be administered to a surgical site.

In some embodiments, components of the device can be fabricated from biologically acceptable materials suitable for medical applications, including metals, synthetic polymers, ceramics and/or their composites. For example, the components of the device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, or any combination thereof.

In some embodiments, lubricants can be added to components of the device or can be added to the bone material. In some embodiments, lubricants can include biological lubricants such as, glycerol, rapeseed, canola, sunflower, soybean, palm oil, coconut oil, sesame seed oil, cottonseed oil, safflower oil, olive oil, almond oil, peanut oil, poppy seed oil and/or castor oil. In some embodiments, the tubular member can include a lubricant layer or layers.

Kit

In various embodiments, the kit may include additional parts along with the device combined together to be used with the particulate bone material (e.g., bone graft) and dilators (e.g., wipes, needles, syringes, etc.). The kit may include the device in a first compartment. The second compartment may include the particulate bone material, along with a mesh or a vial containing diluent and any other delivery instruments (e.g., cannula, plunger, etc.) needed for the localized implant delivery. A third compartment may include a funnel, gloves, drapes, wound dressings and other procedural supplies for maintaining sterility of the implanting process, as well as an instruction booklet, which may include a chart that shows how to implant the bone material. A fourth compartment may include additional needles, fasteners, and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Bone Material

The bone material has a particle size that is greater than the pore size of the tubular member when the tubular member is porous. In some embodiments, the tubular member can be non-porous however, the cap can have a plurality of pores that are smaller than the particle size of the bone material. In this way, the tubular member and/or the cap can allow fluid flow to hydrate the bone material.

In some embodiments, the bone material can be made from natural bone and/or synthetic bone. In various embodiments, the bone material may be particulated such as, for example, in bone chips, powder or fiber form. In some embodiments, the particulate bone material is in a powder or a wet form and has a particle size of 250 microns or less. In some embodiments, the particulate bone material has a particle size of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and/or 250 microns. In some embodiments, the particulate bone material is demineralized bone (DBM).

If the bone is demineralized, the bone may be made into a particulate before, during or after demineralization. In some embodiments, the bone may be monolithic and may not be a particulate.

The bone may be milled and ground or otherwise processed into particles of an appropriate size before or after demineralization. The particles may be particulate (for example, powder) or fibrous. The terms milling or grinding are not intended to be limited to production of particles of a specific type and may refer to production of particulate or fibrous particles. In certain embodiments, the particle size may be greater than 25 microns, such as ranging from about 25 to about 250 microns, or from about 25 to about 200 microns or from about 25 to about 150 microns.

After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone material comprises DBM and/or mineralized bone. In some embodiments, the size of the bone material is less than 25, 50, 75, 100, 125, 150, 175, 200 or 250 microns.

Following shaving, milling or other technique whereby they are obtained, the bone material is subjected to demineralization in order to reduce its inorganic content to a very low level, in some embodiments, to not more than about 5% by weight of residual calcium and to not more than about 1% by weight of residual calcium. Demineralization of the bone material ordinarily results in its contraction to some extent.

Bone used in the methods described herein may be autograft, allograft, or xenograft. In various embodiments, the bone may be cortical bone, cancellous bone, or corticocancellous bone. While specific discussion is made herein to demineralized bone matrix, bone matrix treated in accordance with the teachings herein may be non-demineralized, demineralized, partially demineralized, or surface demineralized. This discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures. For example, in a preferred demineralization procedure, the bone materials useful for the implantable composition of this application are subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection, buffered with a buffering agent to a final predetermined and then finally rinsed with water for injection to remove residual amounts of acid and buffering agent or washed with water to remove residual acid and thereby raise the pH. Following demineralization, the bone material is immersed in solution to effect its defatting. A defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The concentration range of the defatting solution is from about 60 to 85 weight percent alcohol or about 70 weight percent alcohol.

Further in accordance with this application, the DBM material can be used immediately for preparation of the bone implant or it can be stored under aseptic conditions, advantageously in a critical point dried state prior to such preparation. In one embodiment, the bone material can retain some of its original mineral content such that the composition is rendered capable of being imaged utilizing radiographic techniques.

In various embodiments, this application also provides bone matrix compositions comprising critical point drying (CPD) fibers. DBM includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis, DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in this application can be prepared from elongated bone fibers which have been subjected to critical point drying (CPD). The elongated CPD bone fibers employed in this application are generally characterized as having relatively high average length to average width ratios, also known as the aspect ratio. In various embodiments, the aspect ratio of the elongated bone fibers is at least from about 50:1 to at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 2.0 mm to about 1 cm. In various embodiments, the average length of the elongated fibers can be from about 3.5 cm to about 6.0 cm and the average width from about 20 mm to about 1 cm. In other embodiments, the elongated fibers can have an average length from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1.

In some embodiments, the chips to fibers ratio is about 90:10, 80:20, 75:25, 70:30, 60:40, 50:50, 40:60, 30:70, 25:75, 20:80 and/or 10:90. In various embodiments, a surface demineralized chips to fibers ratio is about 90:10, 80:20, 75:25, 70:30, 60:40, 50:50, 40:60, 30:70, 25:75, 20:80 and/or 10:90. In some embodiments, a surface demineralized chips to fully demineralized fibers ratio is about 90:10, 80:20, 75:25, 70:30, 60:40, 50:50, 40:60, 30:70, 25:75, 20:80 and/or 10:90.

In some embodiments, the DBM fibers have a thickness of about 0.5-4 mm. In various embodiments, the DBM fibers have a thickness of about 0.5, 0.6, 0.7, 0.8, 0.9, 1, 1.5, 2, 2.5, 3, 3.5 and/or 4 mm. In various embodiments, the ratio of DBM fibers to DBM powder is about 40:60 to about 90:10 W/W, W/V or V/V. In some embodiments, the ratio of mineralized bone fibers to DBM powder is about 25:75 to about 75:25 W/W, W/V or V/V. In various embodiments, the bone implant comprises DBM fibers and mineralized fibers in a ratio of 40:60 to about 90:10 W/W, W/V or V/V. In some embodiments, the DBM fibers to DBM powder ratio, mineralized bone fibers to DBM powder ratio and/or the DBM fibers and mineralized fibers ratio is from 5:95 to about 95:5 W/W, W/V or V/V. In some embodiments, the DBM fibers to DBM powder ratio, mineralized bone fibers to DBM powder ratio and/or the DBM fibers and mineralized fibers ratio is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 W/W, W/V or V/V.

In some embodiments, the bone material comprises demineralized bone material comprising demineralized bone, fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In various embodiments, the bone material comprises fully DBM fibers and surface demineralized bone chips. In some embodiments, the ratio of fully DBM fibers to surface demineralized bone chips is from 5:95 to about 95:5 fibers to chips. In some embodiments, the ratio of fully DBM fibers to surface demineralized bone chips is 5:95, 10:90, 15:85, 20:80, 25:75, 30:70, 35:65, 40:60, 45:55, 50:50, 55:45, 60:40, 65:35, 70:30, 75:25, 80:20, 85:15, 90:10 and/or 95:5 fibers to chips. In various embodiments, the fully DBM fibers have a thickness of about 0.5-4 mm. In various embodiments, the fully DBM fibers have a thickness of about 0.5, 0.6, 0.7, 0.8, 0.9, 1, 1.5, 2, 2.5, 3, 3.5 and/or 4 mm.

In various embodiments, the fibers and/or the powder is surface DBM. In some embodiments, the fibers and/or the powder is surface DBM cortical allograft. In various embodiments, surface demineralization involves surface demineralization to at least a certain depth. For example, the surface demineralization of the allograft can be from about 0.25 mm, 0.5 mm, 1 mm, 1.5 mm, 2.0 mm, 2.5 mm, 3.0 mm, 3.5 mm, 4 mm, 4.5 mm, to about 5 mm. The edges of the bone fibers and/or powder may further be machined into any shape or to include features such as grooves, protrusions, indentations, etc., to help improve fit and limit any movement or micromotion to help fusion and/or osteoinduction to occur.

To prepare the osteogenic DBM, a quantity of fibers is combined with a biocompatible carrier to provide a demineralized bone matrix.

DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using a critical point drying technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound by a particular theory, this deformation and structure is thought to occur because as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

Mesh Formulations

In some embodiments, the tubular member comprises a mesh and/or a straw. In some embodiments, the mesh can be made from a natural and/or synthetic material such as, for example, poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone, polydioxanone (PDO), allogeneic collagen, xenogenic collagen, metals such as titanium/titanium alloys, TiNi (shape memory/super elastic), aluminum oxide, platinum/platinum alloys, stainless steels, and other metal alloys known to be useful for medical devices, pyrolytic carbon, silver or glassy carbon; polymers such as polyurethanes, polycarbonates, silicone elastomers, polyolefins including polyethylenes or polypropylenes (such as found in hernia mesh substrates and suture materials), polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, ethylene tetrafluoroethylene copolymer (ETFE), acrylonitrile butadiene ethylene, polyamide, polyimide, styrene acrylonitrile, and the like; minerals or ceramics such as hydroxapatite; human or animal protein or tissue such as bone, skin, teeth, collagen, laminin, elastin or fibrin; organic materials such as wood, cellulose, or compressed carbon; and other materials such as glass or a combination thereof.

The mesh can be made from yarn that is monofilament or multi filament, and the mesh can be fabricated using knitting, weaving, non-woven, such as felted or point-bonded, or with additive manufacturing methods (e.g., 3D printing). The mesh can be made of yarn that is monofilament or multifilament, and the yarn can be knitted, woven, non-woven shape memory, felted, point-bonded, additive manufactured, such as 3-D printed or a combination thereof. A weave pattern can be selected to impart flexibility and stretchable characteristics to the mesh.

The mesh can have a weave density of from about 8 to about 400 filaments, such as fibers per inch. The mesh can have a weave density from about 8 to about 375 filaments fibers per inch, from about 8 to about 350 fibers per inch, from about 8 to about 300 fibers per inch, from about 8 to about 250 fibers per inch, from about 8 to about 200 fibers per inch, from about 20 to about 350 fibers per inch, from about 20 to about 300 fibers per inch, from about 20 to about 250 fibers per inch, from about 20 to about 200 fibers per inch, from about 50 to about 350 fibers per inch, from about 50 to about 300 fibers per inch, from about 50 to about 250 fibers per inch, from about 50 to about 200 fibers per inch, from about 100 to about 350 fibers per inch, from about 100 to about 300 fibers per inch, from about 100 to about 250 fibers per inch, or from about 100 to about 200 fibers per inch. The mesh can have a weave density from about 8, 10, 15, 20, 25, 30, 35, 40, 45, 50, 55, 60, 65, 70, 75, 80, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345 to about 350 fibers per inch.

The average molecular weight of the polymer used to make the mesh can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons.

The mesh may have varying degrees of permeability. It may be permeable, semi-permeable, or non-permeable throughout, or in discrete locations. Permeability may be with respect to cells, to liquids, to proteins, to growth factors, to bone morphogenetic proteins, or other substances. The mesh may be 1 to about 30% permeable, from about 30 to about 70% permeable, or from about 70 to about 95% permeable. The mesh may be 1, 5, 10, 15, 20, 25, 30, 35, 40, 45, 50, 55, 60, 65, 70, 75, 80, 85, 90, 95, 96, 97, 98, or 99% permeable.

In some embodiments, the mesh can be made from threads and can have a predetermined thickness of about 0.01 mm to about 2.0 mm, about 0.05 mm to about 1.0 mm, or about 0.1 to about 0.5 mm. The thickness of the threads may be uniform along the length of each thread, or varied across the length of each thread. In some embodiments, some threads have a greater thickness than other threads. The threads may be sized to allow for customizable pore sizes between the threads.

Suitable adhesives for use for closing the mesh material may include, for example, cyanoacrylates (such as histoacryl, B Braun, which is n-butyl-2 cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; for example, in some circumstances, a temporary adhesive may be desirable, while in other circumstances a permanent adhesive may be desired. In some embodiments, the mesh material can be closed via heat sealing or sonic welding techniques.

In accordance with some embodiments, the particulate bone material to be loaded in the tubular member may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anti-coagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh material. Functional characteristics may include radiopacity, bacteriocidity, source for released materials, tackiness, etc. Such characteristics may be imparted substantially throughout the mesh material and/or mesh body or at only certain positions or portions of the mesh material and/or mesh body.

Suitable radiopaque materials that can be added to the particulate bone material include, for example, ceramics, mineralized bone, ceramics/calcium phosphates/calcium sulfates, metal particles, fibers, and iodinated polymer (see, for example, WO/2007/143698). Suitable bacteriocidal materials may include, for example, trace metallic elements. In some embodiments, trace metallic elements may also encourage bone growth.

Methods

A method of hydrating particulate bone material is provided. The devices and particulate bone material used in this method can be found in FIGS. 1-12. The method can be employed with various delivery instrument and in a surgical treatment with a patient in a prone or supine position, and/or employ various surgical approaches to the spine, including anterior, posterior, posterior mid-line, direct lateral, and/or antero-lateral approaches, and in other body regions. The method may also be employed with procedures for treating the lumbar, cervical, thoracic, sacral and pelvic regions of a spinal column. The method may also be used on animals, bone models and other non-living substrates, such as, for example, in training, testing and demonstration.

The method comprises loading a device for hydrating the particulate bone material, the device comprising a tubular member having an interior surface and an exterior surface, the interior surface configured to receive the particulate bone material and a hydration fluid, the exterior surface having a plurality of pores configured to allow the hydration fluid to flow into the interior surface of the tubular member and hydrate the particulate bone material, the plurality of pores being smaller in size than the particulate bone material; immersing the device in a fluid filled bath; and engaging the device with a cannula and a plunger to dispense the particulate bone material to the surgical site.

In some embodiments, the proximal end opening of the tubular member comprises a collar configured to engage the cannula, or a proximal end of the cannula comprises a collar configured to engage the tubular member.

In some embodiments, the tubular member comprises a removable distal end configured to form a distal end opening to dispense the particulate bone material.

The bone material may be used in a minimally invasive procedure via placement through a small incision, via delivery through the dilators, or other means. The size and shape may be designed with restrictions on delivery conditions. For example, the bone material may be percutaneously delivered to the surgical site, and in some cases, the surgical site is the posterior spine.

In some embodiments, the bone material may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others.

Generally, the bone material may be applied to a pre-existing defect, to a created channel, or to a modified defect. Thus, for example, a channel may be formed in a bone, or a pre-existing defect may be cut to form a channel, for receipt of the bone material. The bone material may be configured to match the channel or defect. In some embodiments, the configuration of bone material may be chosen to match the channel. In other embodiments, the channel may be created, or the defect expanded or altered, to reflect a configuration of the bone material. The bone material may be placed in the defect or channel and, optionally, coupled using attachment mechanisms.

Although the invention has been described with reference to embodiments, persons skilled in the art will recognize that changes may be made in form and detail without departing from the spirit and scope of the invention.

What is claimed is:

1. A device for hydrating particulate bone material, the device comprising a tubular member having an interior surface and an exterior surface, the interior surface configured to receive the particulate bone material and a hydration fluid, the exterior surface having a plurality of pores configured to allow the hydration fluid to flow into the interior surface of the tubular member and hydrate the particulate bone material, the plurality of pores being smaller in size than the particulate bone material, wherein the tubular member comprises a port configured to receive a syringe, wherein the plurality of pores disposed on the exterior surface of the tubular member are configured to directly contact the hydration fluid and be immersed in the hydration fluid such that the syringe moves to create a negative pressure within the tubular member and the hydration fluid is allowed to pass through the plurality of pores into the syringe through the port.

2. The device of claim 1, wherein (i) the tubular member comprises a proximal end opening configured to receive the particulate bone material; (ii) the tubular member comprises a distal end opening configured to dispense the particulate bone material; (iii) or a combination thereof.

3. The device of claim 2, wherein the tubular member is configured to slidably engage a cannula and the proximal end opening of the tubular member is configured to slidably receive a plunger.

4. The device of claim 3, wherein the proximal end opening of the tubular member comprises a collar configured to engage the cannula, or a proximal end of the cannula comprises a collar configured to engage the tubular member.

5. The device of claim 4, wherein the collar is a rigid funnel.

6. The device of claim 1, wherein the tubular member comprises a removable distal end configured to form a distal end opening to dispense the particulate bone material.

7. The device of claim 1, wherein the tubular member comprises a mesh or a straw.

8. The device of claim 1, wherein the tubular member is moldable or flexible.

9. The device of claim 1, wherein the plurality of pores have a pore size from about 10 to about 100 microns.

10. The device of claim 1, wherein the tubular member comprises a one-way valve.

11. The device of claim 10, wherein the interior surface of the tubular member at a proximal end comprises threading to engage with a threaded outer surface of a plunger.

12. The device of claim 1, wherein the port is disposed perpendicular to the tubular member.

13. The device of claim 1, wherein (i) the particulate bone material is in a powder or a wet form; (ii) the particulate bone material has a particle size of 250 microns or less; or (iii) the particulate bone material is demineralized bone (DBM).

14. A method of dispensing particulate bone material at a surgical site, the method comprising loading a device for hydrating the particulate bone material, the device comprising a tubular member having an interior surface and an exterior surface, the interior surface configured to receive the particulate bone material and a hydration fluid, the exterior surface having a plurality of pores configured to allow the hydration fluid to flow into the interior surface of the tubular member and hydrate the particulate bone material, the plurality of pores being smaller in size than the particulate bone material; immersing the device in a fluid filled bath; and engaging the device with a cannula and a plunger to dispense the particulate bone material to the surgical site, wherein the tubular member comprises a port configured to receive a syringe.

15. The method of claim 14, wherein a proximal end opening of the tubular member comprises a collar configured to engage the cannula, or a proximal end of the cannula comprises a collar configured to engage the tubular member.

16. The method of claim 14, wherein the tubular member comprises a removable distal end configured to form a distal end opening to dispense the particulate bone material.

* * * * *